United States Patent
Kojima et al.

(10) Patent No.: US 10,729,309 B2
(45) Date of Patent: Aug. 4, 2020

(54) ENDOSCOPE SYSTEM

(71) Applicant: OLYMPUS CORPORATION, Tokyo (JP)

(72) Inventors: Koji Kojima, Hachioji (JP); Hideyuki Kugimiya, Hachioji (JP); Ryo Koshida, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/401,186

(22) Filed: May 2, 2019

(65) Prior Publication Data

US 2019/0254501 A1 Aug. 22, 2019

Related U.S. Application Data

(63) Continuation of application No. PCT/JP2017/038502, filed on Oct. 25, 2017.

(30) Foreign Application Priority Data

Nov. 8, 2016 (JP) .................................. 2016-218318

(51) Int. Cl.
*H04N 13/00* (2018.01)
*H04N 7/18* (2006.01)
(Continued)

(52) U.S. Cl.
CPC ............ *A61B 1/00009* (2013.01); *A61B 1/00* (2013.01); *A61B 1/04* (2013.01); *A61B 1/045* (2013.01);
(Continued)

(58) Field of Classification Search
CPC ......... A61B 1/00009; A61B 1/00; A61B 1/04; A61B 1/045; A61B 1/0676; A61B 1/0002;
(Continued)

(56) References Cited

U.S. PATENT DOCUMENTS 7,671,888 B2 * 3/2010 Nogami ............... A61B 1/0005
348/45
2016/0029011 A1 1/2016 Mizoguchi et al.
2016/0269713 A1 9/2016 Kasumi et al.

FOREIGN PATENT DOCUMENTS

JP H08-015616 A 1/1996
JP 5784847 B2 9/2015
(Continued)

OTHER PUBLICATIONS

International Search Report dated Jan. 23, 2018 issued in PCT/JP2017/038502.

*Primary Examiner* — Sherrie Hsia
(74) *Attorney, Agent, or Firm* — Scully, Scott, Murphy & Presser, P.C.

(57) ABSTRACT

An endoscope system includes: a first processor configured to perform first image processing on a set of image data; a second processor configured to perform second image processing on another set of image data; a third processor configured to generate, based on sets of image data output from the first and second processors, display image data; a recorder configured to record therein image data based on the sets of image data output from the first and second processors; a fourth processor configured to generate a first synchronization signal for synchronization among the first processor, the second processor, and the third processor; a fifth processor configured to generate a second synchronization signal for synchronization between the third processor and the recorder; and a controller configured to select one of the first and second synchronization signals, and perform control for synchronization between the third processor and the recorder.

3 Claims, 5 Drawing Sheets

(51) Int. Cl.
  *A61B 1/04*    (2006.01)
  *A61B 1/00*    (2006.01)
  *H04N 13/204*   (2018.01)
  *A61B 1/045*    (2006.01)
  *A61B 1/06*    (2006.01)
  *G02B 23/24*   (2006.01)
  *H04N 5/225*    (2006.01)

(52) U.S. Cl.
  CPC ............ *A61B 1/0676* (2013.01); *G02B 23/24* (2013.01); *G02B 23/2415* (2013.01); *H04N 7/18* (2013.01); *H04N 13/204* (2018.05); *A61B 1/0002* (2013.01); *A61B 1/00045* (2013.01); *G02B 23/2484* (2013.01); *G06T 2207/10068* (2013.01); *H04N 2005/2255* (2013.01)

(58) Field of Classification Search
  CPC ...... A61B 1/00045; G06T 2207/10068; G02B 23/2415; G02B 23/24; G02B 23/2484; H04N 13/189; H04N 13/398; H04N 13/10; H04N 13/167; H04N 13/204; H04N 7/18; H04N 2005/2255
  USPC ..................... 348/65, 45, 82, 66, 68, 69, 74; 356/241.1, 241.4; 385/117; 600/101, 600/109, 111, 160, 166
  See application file for complete search history.

(56) References Cited

FOREIGN PATENT DOCUMENTS

| | | |
|---|---|---|
| WO | WO 2009/131840 A1 | 10/2009 |
| WO | WO 2015/111263 A1 | 7/2015 |

\* cited by examiner

ENDOSCOPE SYSTEM

CROSS-REFERENCE TO RELATED APPLICATION

This application is a continuation of PCT International Application No. PCT/JP2017/038502 filed on Oct. 25, 2017, which designates the United States, incorporated herein by reference, and which claims the benefit of priority from Japanese Patent Application No. 2016-218318, filed on Nov. 8, 2016, incorporated herein by reference.

BACKGROUND

1. Technical Field

The present disclosure relates to an endoscope system.

2. Related Art

There is a demand for an observation target to be observed as a stereoscopic image for facilitation of diagnosis and examination with an endoscope system, which is used in the medical field and the like, and in which an endoscope and processors are attachable and detachable from each other. Known as a technique for meeting this demand is an endoscope system including an endoscope that generates sets of image data respectively for left eye and for right eye, and a mixer unit that generates a parallax image from an image for left eye and an image for right eye that have been generated by the endoscope (for example, see Japanese Patent No. 5784847).

FIG. 6 is a diagram illustrating a schematic configuration of a conventional endoscope system. An endoscope system 100 illustrated in FIG. 6 includes: two optical systems for left eye and for right eye; an endoscope 101 having two imaging elements that generate sets of image data for left eye and for right eye respectively via the two optical systems; a first processor 102 that acquires one of the sets of image data for left eye and for right eye and performs image processing on the acquired one of the sets of image data; a second processor 103 that acquires the other one of the sets of image data for left eye and for right eye and performs image processing on the acquired other one of the sets of image data; a mixer unit 104 that generates a parallax image from an image for left eye and an image for right eye that have been subjected to the image processing respectively by the first processor 102 and the second processor 103; a light source device 105 that supplies illumination light to the endoscope 101; and a display device 106 that displays thereon the parallax image generated by the mixer unit 104.

In the conventional system as illustrated in FIG. 6, the first processor 102, the second processor 103, and the mixer unit 104 are synchronized with one another, for example, by a synchronization signal generated by the mixer unit 104.

SUMMARY

In some embodiments, an endoscope system includes: a first processor configured to perform first image processing on a set of image data, and output the set of image data that has been subjected to the first image processing, the set of image data being one of: two sets of image data having object image acquisition areas that are at least partially different from each other; or two sets of image data having a parallax from each other for a common object; a second processor configured to perform second image processing on another set of image data, and output the other set of image data that has been subjected to the second image processing, the other set of image data being other one of: the two sets of image data having the object image acquisition areas that are at least partially different from each other; or the two sets of image data having the parallax from each other for the common object; a third processor that is provided in a housing separately bodied from a housing or housings where the first processor and the second processor are provided, the third processor being configured to generate, based on the set of image data output from the first processor and on the other set of image data output from the second processor, display image data to be displayed on a display; a recorder configured to record therein image data based on the set of image data output from the first processor and on the other set of image data output from the second processor; a fourth processor that is provided in the housing where the first processor or the second processor is provided, the fourth processor being configured to generate a first synchronization signal for synchronization among the first processor, the second processor, and the third processor; a fifth processor that is provided in the housing where the third processor is provided, the fifth processor being configured to generate a second synchronization signal for synchronization between at least the third processor and the recorder; and a controller configured to select one of the first synchronization signal generated by the fourth processor and the second synchronization signal generated by the fifth processor, and perform control for synchronization between the third processor and the recorder.

The above and other features, advantages and technical and industrial significance of this disclosure will be better understood by reading the following detailed description of presently preferred embodiments of the disclosure, when considered in connection with the accompanying drawings.

DETAILED DESCRIPTION

Described hereinafter are modes (hereinafter, referred to as "embodiments") for carrying out the disclosure. Medical endoscope systems for capturing and displaying in-vivo images of subjects, such as patients, will be described as embodiments that are examples of an endoscope system according to the disclosure. Furthermore, the disclosure is not limited by these embodiments. Moreover, each part will be assigned with the same reference sign throughout the drawings and description.

First Embodiment

Figure 1:
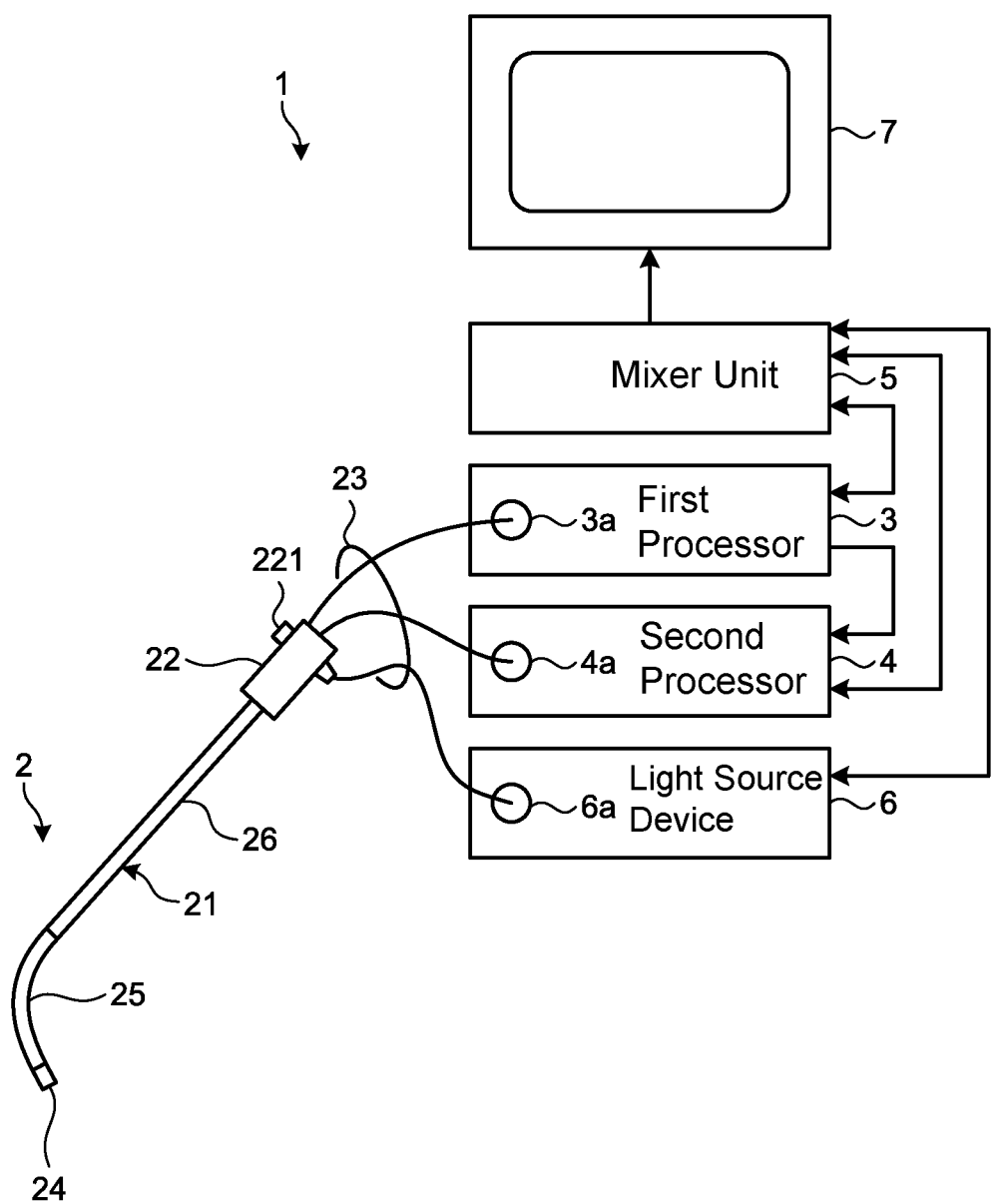
FIG. 1 is a diagram illustrating a schematic configuration of an endoscope system according to a first embodiment of the disclosure.
Figure 2:
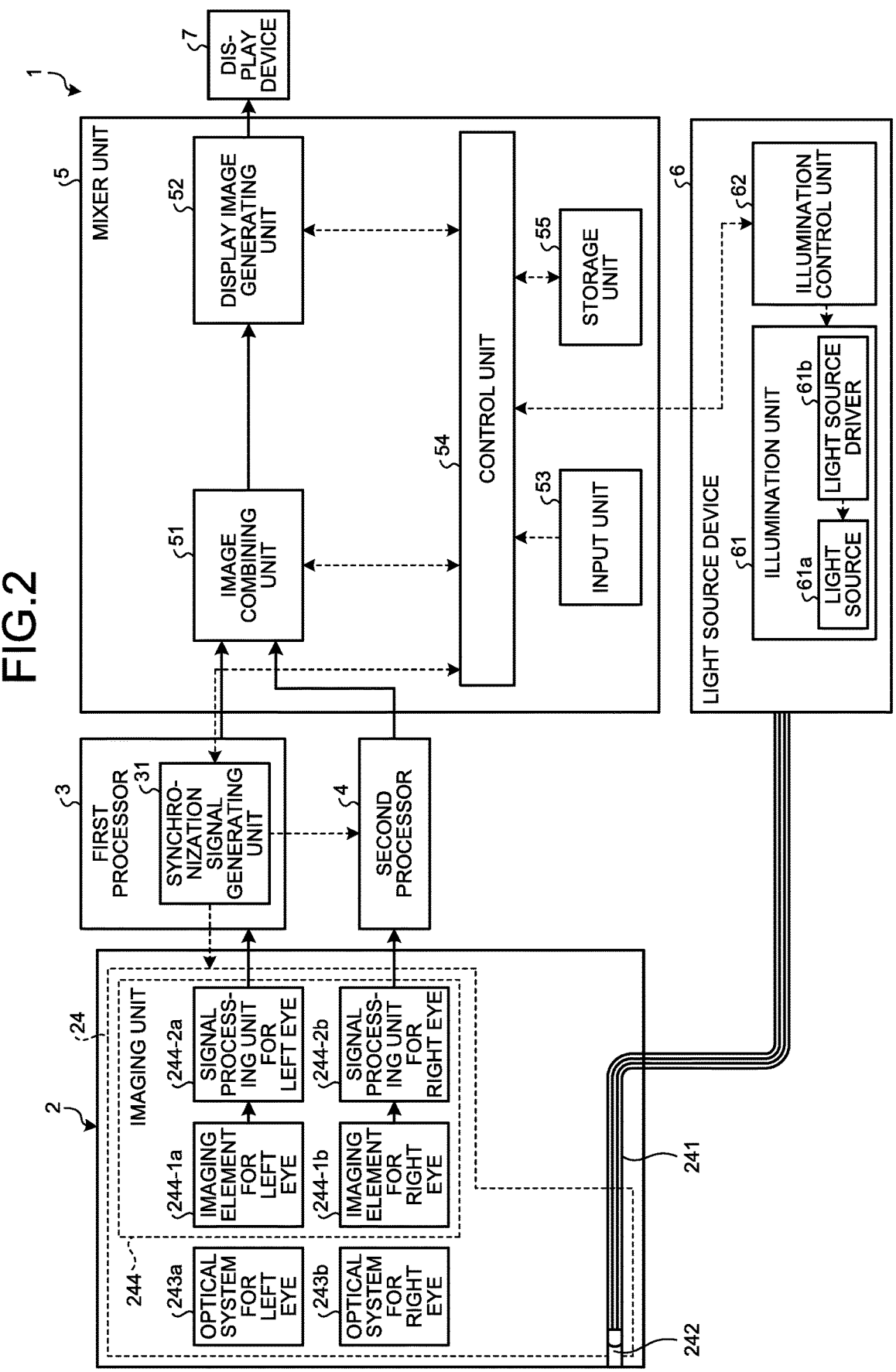
FIG. 2 is a block diagram illustrating a schematic configuration of the endoscope system according to the first embodiment of the disclosure.

FIG. 1 is a diagram illustrating a schematic configuration of an endoscope system according to a first embodiment of the disclosure. FIG. 2 is a block diagram illustrating a schematic configuration of the endoscope system according to the first embodiment.

An endoscope system 1 illustrated in FIG. 1 and FIG. 2 includes: an endoscope 2, which is for capturing an in-vivo image (hereinafter, also referred to as an endoscopic image) of a subject by insertion of a distal end portion of the endoscope 2 into the subject, and which generates sets of image data for left eye and for right eye for generating a parallax image; a first processor 3, which acquires one of the sets of image data for left eye and for right eye generated by the endoscope 2, and performs image processing on the acquired one of the sets of image data; a second processor 4, which acquires the other one of the sets of image data for left eye and for right eye generated by the endoscope 2, and performs image processing on the acquired other one of the sets of image data; a mixer unit 5 that generates a parallax image from an image for left eye and an image for right eye that have been subjected to the image processing by the first processor 3 and the second processor 4 respectively; a light source device 6 that supplies illumination light to the endoscope 2; and a display device 7 that displays thereon the parallax image generated by the mixer unit 5. In FIG. 2, solid lined arrows represent transmission of electric signals related to images, and broken lined arrows represent transmission of electric signals related to control and synchronization.

The endoscope 2 includes: an insertion unit 21 that has flexibility and is elongated; an operating unit 22 that is connected to a proximal end of the insertion unit 21 and receives input of various operation signals; and a cable unit 23 that extends in a direction different from a direction in which the insertion unit 21 extends from the operating unit 22, the cable unit 23 being formed of various cables connected respectively to the first processor 3, the second processor 4, and the light source device 6.

The insertion unit 21 has: a distal end portion 24 having an imaging unit 244 built therein, the imaging unit 244 having two-dimensionally arranged pixels that generate signals by receiving light and photoelectrically converting the light; a bending portion 25 that is formed of plural bending pieces and is freely bendable; and a flexible tube portion 26 that is connected to a proximal end of the bending portion 25, has flexibility, and is elongated. The insertion unit 21 is inserted into a body cavity of the subject, and captures, through the imaging unit 244, an image of an object, such as a living tissue that is present at a position where external light is unable to reach.

The distal end portion 24 has: a light guide 241 that is formed by use of glass fiber or the like and forms a light guiding path for light emitted by the light source device 6; an illumination lens 242 provided at a distal end of the light guide 241; an optical system for left eye 243a and an optical system for right eye 243b, which are for condensing light; and the imaging unit 244 that receives light condensed by the optical system for left eye 243a and the optical system for right eye 243b, photoelectrically converts the light into electric signals, and performs predetermined signal processing on the electric signals.

The optical system for left eye 243a is formed by use of one or plural lenses, is provided upstream of the imaging unit 244, and forms an image of light incident thereon from the object. The optical system for left eye 243a may have an optical zooming function for changing the angle of view; and a focusing function for changing the focus.

The optical system for right eye 243b is formed by use of one or plural lenses, is provided upstream of the imaging unit 244, and forms an image of light incident thereon from the object, the image having a parallax from that of the optical system for left eye 243a. The optical system for right eye 243b may have an optical zooming function for changing the angle of view and a focusing function for changing the focus.

The imaging unit 244 includes an imaging element for left eye 244-1a, an imaging element for right eye 244-1b, a signal processing unit for left eye 244-2a, and a signal processing unit for right eye 244-2b.

According to a control signal received from the mixer unit 5, the imaging element for left eye 244-1a photoelectrically converts light from the optical system for left eye 243a, and generates electric signals (a set of image data for left eye) corresponding to one frame forming a single image. Specifically, the imaging element for left eye 244-1a has plural pixels arranged in a matrix, each of the plural pixels having a photodiode that accumulates therein electric charge according to quantity of light, a condenser that converts an electric charge transferred from the photodiode into a voltage level, and the like; each of the plural pixels generates an electric signal by photoelectrically converting light from the optical system for left eye 243a; and electric signals generated by pixels arbitrarily set as targets to be read, from among the plural pixels, are sequentially read out and output as a set of image data. Exposure processing by the imaging element for left eye 244-1a is controlled, based on a control signal received from the mixer unit 5. The imaging element for left eye 244-1a has color filters provided on a light receiving surface thereof, and each pixel receives light of one of wavelength bands of red (R), green (G), and blue (B) color components.

According to a control signal received from the mixer unit 5, the imaging element for right eye 244-1b photoelectrically converts light from the optical system for right eye 243b, and generates electric signals (a set of image data for right eye) corresponding to one frame forming a single image. Specifically, the imaging element for right eye 244-1b has plural pixels arranged in a matrix, each of the plural pixels having a photodiode that accumulates therein electric charge according to quantity of light, a condenser that converts an electric charge transferred from the photodiode into a voltage level, and the like; each of the plural pixels generates an electric signal by photoelectrically converting light from the optical system for right eye 243b; and electric signals generated by pixels arbitrarily set as targets to be read, from among the plural pixels, are sequentially read out and output as a set of image data. Exposure processing by the imaging element for right eye 244-1b is controlled, based on a control signal received from the mixer unit 5. The imaging element for right eye 244-1b has color filters provided on a light receiving surface thereof, and each pixel receives light of one of wavelength bands of red (R), green (G), and blue (B) color components.

The imaging element for left eye 244-1a and the imaging element for right eye 244-1b are each realized by use of, for example, a charge coupled device (CCD) image sensor, or a complementary metal oxide semiconductor (CMOS) image sensor. Furthermore, the imaging element for left eye 244-1a and the imaging element for right eye 244-1b may each be formed by use of a single image sensor, or formed by use of plural image sensors, such as, for example, three image sensors.

An image for left eye acquired by the imaging element for left eye 244-1a and an image for right eye acquired by the imaging element for right eye 244-1b are images having: a common object captured therein; different object image acquisition areas; and a parallax from each other. If optical axes of the optical system for left eye 243a and the optical system for right eye 243b have different angles relatively to the object, their object image acquisition areas (portions captured as images) also differ from each other.

The signal processing unit for left eye 244-2a performs analog processing for performing noise removal processing and clamp processing on a set of analog image data for left eye output from the imaging element for left eye 244-1a and A/D conversion processing for performing A/D conversion processing thereon, and outputs a set of digital image data for left eye including an image for left eye, to the first processor 3.

The signal processing unit for right eye 244-2b performs analog processing for performing noise removal processing and clamp processing on a set of analog image data for right eye output from the imaging element for right eye 244-1b and A/D conversion processing for performing A/D conversion processing thereon, and outputs a set of digital image data for right eye including an image for right eye, to the second processor 4.

The operating unit 22 has plural switches 221 that are operation input units, through which operation instruction signals are input, the operation instruction signals being for, in addition to the mixer unit 5, a gas feeding means, a water feeding means, and a peripheral device for screen display control and the like. The operating unit 22 may have, provided therein: a bending knob that bends the bending portion 25 upward, downward, leftward, and rightward; and a surgical tool insertion portion, through which surgical tools, such as biopsy forceps, an electric knife, and an examination probe, are inserted into the body cavity of the subject. A surgical tool inserted from the surgical tool insertion portion comes out from an opening (not illustrated in the drawings) via a surgical tool channel of the distal end portion 24.

The cable unit 23 has at least: the light guide 241; a cable assembly having one or plural signal lines that are connected to the first processor 3 and are assembled together; and a cable assembly having one or plural signal lines that are connected to the second processor 4 and are assembled together. Each of the cable assemblies includes a signal line for transmitting image data, a signal line for transmitting a control signal and a synchronization signal for controlling the imaging unit 244, and a signal line for transmitting and receiving information including specific information and the like related to the endoscope 2 (imaging unit 244). The cable unit 23 is electrically connected to the first processor 3 and the second processor 4 via a connector unit 3a of the first processor 3 and a connector unit 4a of the second processor 4, and the light guide 241 is connected to the light source device 6 via a connector unit 6a of the light source device 6. According to the description of this embodiment, an electric signal is transmitted by use of a signal line; but an optical signal may be transmitted or a signal may be transmitted between the endoscope 2 and the first processor or second processor 4 via wireless communication, instead.

Furthermore, the endoscope 2 has a memory (not illustrated in the drawings) having information on the endoscope 2, recorded therein. This memory has, recorded therein, identification information indicating a type and a model number of the endoscope 2, types of the imaging element for left eye 244-1a and imaging element for right eye 244-1b, and the like. The memory may have various parameters recorded therein, the various parameters being for image processing on sets of image data captured by the imaging element for left eye 244-1a and the imaging element for right eye 244-1b, such as parameters for white balance (WB) adjustment.

The first processor 3 receives a set of image data for left eye from the imaging unit 244 of the endoscope 2, and performs image processing on the received image data for left eye. The first processor 3 calculates, for each pixel position in the set of image data for left eye, a pixel value of a luminance component (for example, a Y component of YCrCB) and a pixel value of each of RGB color components, and performs signal processing thereon, such as defective pixel correction, optical correction, color correction, optical black subtraction, noise reduction, white balance adjustment, and interpolation processing. In the defective pixel correction, a pixel value of a defective pixel is assigned based on pixel values of pixels around the defective pixel. In the optical correction, correction of optical distortion of the lens or the like is performed. In the color correction, correction of color temperature and correction of color deviation are performed. The first processor 3 is formed by use of a general-purpose processor, such as a central processing unit (CPU), or a special-purpose processor, such as an arithmetic circuit that executes a specific function, like an application specific integrated circuit (ASIC) or a field programmable gate arrays (FPGA), which is a programmable logic device for which the processing content is rewritable.

Furthermore, the first processor 3 has a synchronization signal generating unit 31. The synchronization signal generating unit 31 generates a clock signal (synchronization signal) serving as a reference for operation of the first processor 3, and outputs the generated synchronization signal to the endoscope 2, the second processor 4, and the mixer unit 5. The synchronization signal generated by the synchronization signal generating unit 31 includes a horizontal synchronization signal and a vertical synchronization signal.

The second processor 4 receives a set of image data for right eye from the imaging unit 244 of the endoscope 2, and performs image processing on the received set of image data for right eye. The second processor 4 calculates, for each pixel position in the set of image data for right eye, a pixel value of a luminance component (for example, a Y component of YCrCB) and a pixel value of each of RGB color components, and performs signal processing thereon, such as defective pixel correction, optical correction, color correction, optical black subtraction, noise reduction, white balance adjustment, and interpolation processing. The second processor 4 operates according to the synchronization signal generated by the synchronization signal generating unit 31 of the first processor 3. The second processor 4 is formed by use of: a general-purpose processor, such as a CPU; or a special-purpose processor, such as an arithmetic circuit that executes a specific function, like an ASIC or an FPGA. According to the first embodiment, the second processor 4 is provided in a housing that is separately bodied from a housing where the first processor 3 is provided.

Described next is a configuration of the mixer unit 5. The mixer unit 5 includes an image combining unit 51, a display image generating unit 52, an input unit 53, a control unit 54, and a storage unit 55.

The image combining unit 51 generates data for one combined image by combining two sets of image data generated respectively by the first processor 3 and the second processor 4. The image combining unit 51 outputs the combined image data generated, to the display image generating unit 52.

Figure 3:
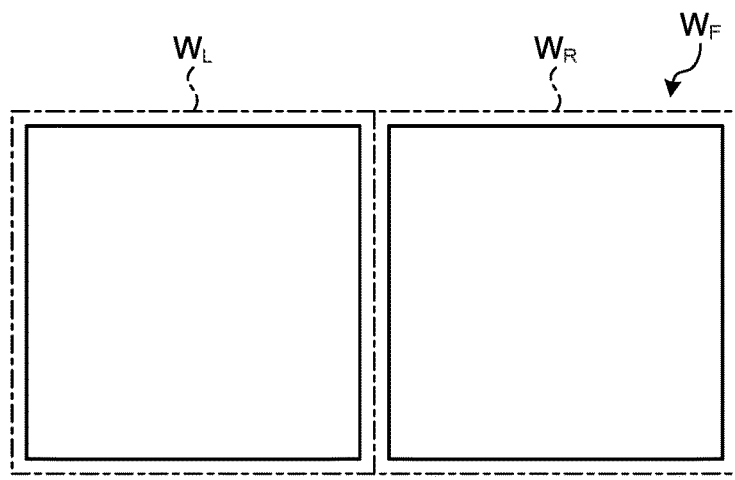
FIG. 3 is a diagram illustrating an example of a combined image combined by an image combining unit of the endoscope system according to the first embodiment of the disclosure.

FIG. 3 is a diagram illustrating an example of a combined image combined by the image combining unit of the endoscope system according to the first embodiment of the disclosure. The image combining unit 51 generates one combined image $W_F$ that has been combined by arranging, as illustrated in FIG. 3, an image for left eye $W_L$ and an image for right eye $W_R$ side by side. The combined image $W_F$ may have the image for left eye $W_L$ and the image for right eye $W_R$ arranged side by side along a horizontal line of the pixel array (see, for example, FIG. 3), or may have the image for left eye $W_L$ and the image for right eye $W_R$ arranged side by side along a vertical line of the pixel array. The image for left eye $W_L$ and the image for right eye $W_R$ are each an image including pixel values of an optical black area outside an effective pixel area.

Figure 4:
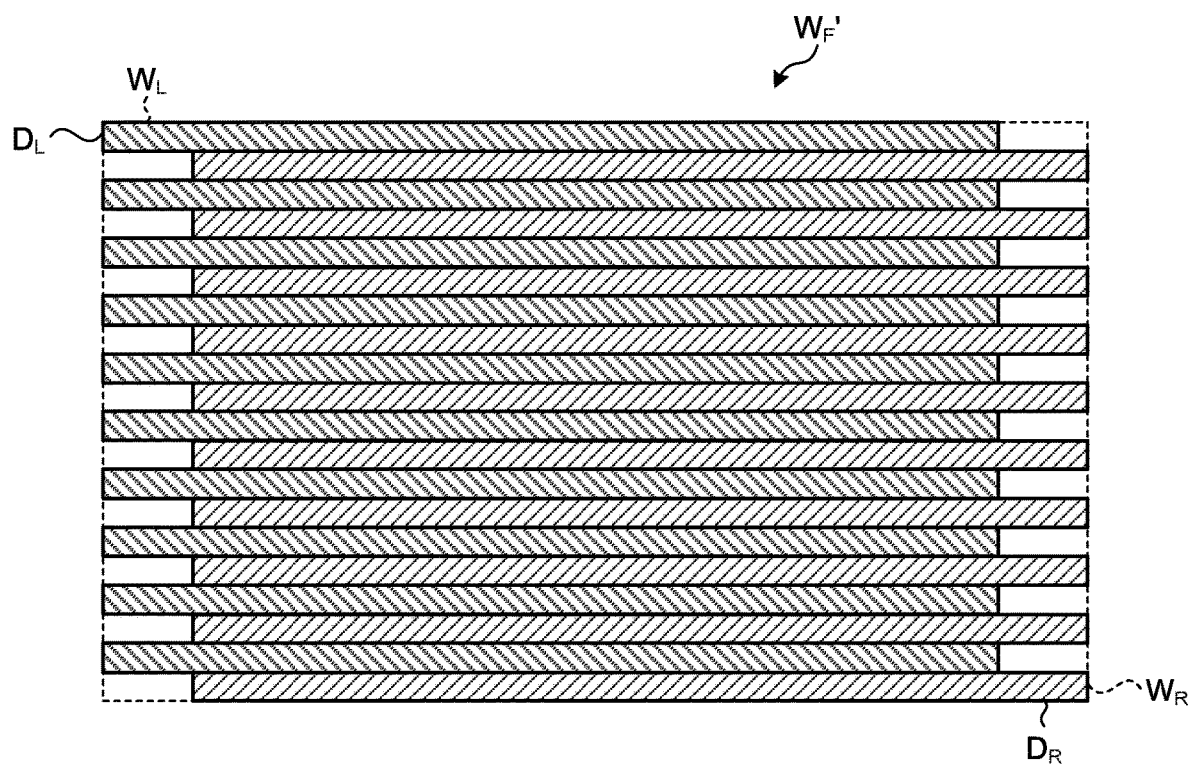
FIG. 4 is a diagram illustrating another example of a combined image combined by the image combining unit of the endoscope system according to the first embodiment of the disclosure.

Instead of arranging the image for left eye $W_L$ and the image for right eye $W_R$ side by side as described above, the image for left eye $W_L$ and the image for right eye $W_R$ may be periodically arranged line by line. FIG. 4 is a diagram illustrating another example of a combined image combined by the image combining unit of the endoscope system according to the first embodiment of the disclosure. As illustrated in FIG. 4, the image combining unit 51 generates a combined image $W_F'$ by periodically arranging line images $D_L$ that are horizontal lines in the image for left eye $W_L$ and line images $D_R$ that are horizontal lines in the image for right eye $W_R$, such that the line images $D_L$ and the line images $D_R$ are displaced from each other according to a set amount of shift. Specifically, the image combining unit 51 alternately arranges the line images $D_L$ of odd lines that the image for left eye $W_L$ has and the line images $D_R$ of even lines that the image for right eye $W_R$ has, such that the line images $D_L$ and the line images $D_R$ are displaced from each other according to the set amount of shift. This combined image $W_F'$ is also called a line-by-line image. A horizontal line referred to herein corresponds to a line formed of pixels arranged along one of array directions in an imaging element having plural pixels arranged in a matrix. The combined image $W_F'$ is formed by combining the image for left eye $W_L$ and the image for right eye $W_R$ into one set of data; and thus the combined image $W_F'$ may even be an image formed by setting the amount of shift to zero and alternately arranging the line images $D_L$ of the image for left eye $W_L$ and the line images $D_R$ of the image for right eye $W_R$, that is, an image having both ends of the line images $D_L$ and line images $D_R$ aligned with each other. Furthermore, the image combining unit 51 may generate a combined image by periodically arranging, line by line, vertical lines that are lines vertical to the horizontal lines.

The display image generating unit 52 generates a composite image including character information related to an endoscopic image, the character information having been composited with a background image including a display area of the endoscopic image. Specifically, the display image generating unit 52 performs composition by: referring to the storage unit 55; and superimposing character information or the like related to an endoscopic image that has been captured, on a background image forming a display screen, for example, a black background.

After generating the composite image that has been subjected to the above described composition processing, the display image generating unit 52 generates image data for display, by performing signal processing on the composite image so as to obtain a signal that is able to be displayed on the display device 7. Specifically, the display image generating unit 52 firstly acquires an image for left eye and an image for right eye in a combined image from the image combining unit 51, and generates a parallax image called a so-called side-by-side image by arranging the image for left eye and image for right eye at positions, which are separate from each other and provide a parallax therebetween. Thereafter, the display image generating unit 52 superimposes the generated parallax image on an image forming a display screen, performs compression processing or the like on image data including the superimposed image, and generates image data for display therefrom. The display image generating unit 52 transmits the generated image data for display, to the display device 7. The display image generating unit 52 does not necessarily generate a side-by-side image, and may generate a line-by-line image obtained by combining a set of line data of an image for left eye and a set of line data of an image for right eye by alternately arranging the sets of line data by displacing the sets of line data from each other by an amount of shift that provides a parallax therebetween.

Furthermore, according to settings set and input via the input unit 53, the display image generating unit 52 may perform zooming processing or enhancement processing on a combined image that has been subjected to the above described image processing. Specifically, the display image generating unit 52 may perform, for example, enhancement processing for enhancing the R-component, if it has been set via the input unit 53 that the red component is to be enhanced.

The image combining unit 51 and the display image generating unit 52 are each formed by use of: a general-purpose processor, such as a CPU; or a special-purpose processor, such as an arithmetic circuit that executes a specific function, like an ASIC or an FPGA.

The input unit 53 is realized by use of a keyboard and a mouse, switches, or a touch panel; and receives input of various signals, such as operation instruction signals for instructing the endoscope system 1 to operate. The input unit 53 may include a switch provided in the operating unit 22, or a portable terminal, such as an external tablet computer.

The control unit 54 performs drive control of the respective units including the imaging unit 244 and the light source device 6, and input and output control of information for the respective units. The control unit 54 transmits, to the imaging unit 244, control information data (for example, a readout timing) for imaging control stored in the storage unit 55, via a predetermined signal line or the first processor 3 or second processor 4, the control information data serving as a control signal. Furthermore, the control unit 54 performs control for causing the display device 7 to display thereon an image for display generated by the display image generating unit 52. The control unit 54 controls operation of each unit according to a synchronization signal generated by the synchronization signal generating unit 31 of the first processor 3. The control unit 54 is formed by use of: a general-purpose processor, such as a CPU; or a special-purpose processor, such as an arithmetic circuit that executes a specific function, like an ASIC.

The storage unit 55 stores therein: various programs for operating the endoscope system 1; data including various parameters needed for the operation of the endoscope system 1; information related to composition processing that is so-called on-screen display (OSD) processing, the composition processing being for generating a composite image having image information that has been subjected to predetermined image processing and character information related to the image information, the image information and the character information having been superimposed on each other; and the like. The character information is information indicating patient information, device information, examination information, and the like. Furthermore, the storage unit 55 stores therein identification information of the mixer unit 5. This identification information includes specific information (ID), the model year, and specification information, of the mixer unit 5.

Furthermore, the storage unit 55 stores therein various programs including an image acquisition processing program for executing an image acquisition processing method by the mixer unit 5. The various programs may be widely distributed by being recorded in a computer readable recording medium, such as a hard disk, a flash memory, a CD-ROM, a DVD-ROM, or a flexible disk. The above described various programs may be acquired by being downloaded via a communication network. The communication network referred to herein is realized by, for example, an existing public network, a local area network (LAN), or a wide area network (WAN), and may be wired or wireless.

The storage unit 55 having the above described configuration is realized by use of: a read only memory (ROM) having the various programs and the like preinstalled therein; and a random access memory (RAM), a hard disk, or the like, which stores therein arithmetic parameters, data, and the like for respective kinds of processing.

The endoscope 2, the second processor 4, and the mixer unit 5 are synchronized with one another according to a synchronization signal generated by the synchronization signal generating unit 31 in the first processor 3. That is, the endoscope 2, the second processor 4, and the mixer unit 5 operate based on the synchronization signal generated by the synchronization signal generating unit 31.

Described next is a configuration of the light source device 6. The light source device 6 includes an illumination unit 61 and an illumination control unit 62. Under control by the illumination control unit 62, the illumination unit 61 emits illumination light. The illumination unit 61 has a light source 61a and a light source driver 61b.

The light source 61a is formed by use of an LED light source that emits white light, and one or plural lenses or the like; and emits light (illumination light) by the LED light source being driven. The illumination light emitted by the light source 61a is emitted to the object from a distal end of the distal end portion 24 via the light guide 241. Furthermore, the light source 61a is realized by use of any of an LED light source, a laser light source, a xenon lamp, a halogen lamp, and the like.

The light source driver 61b causes the light source 61a to emit illumination light by supplying electric power to the light source 61a, under control by the illumination control unit 62.

Based on a control signal (light control signal) from the control unit 54, the illumination control unit 62 controls the amount of electric power to be supplied to the light source 61a and controls the drive timing for the light source 61a.

The display device 7 displays thereon an image for display corresponding to image data received from the mixer unit 5 (display image generating unit 52) via a video cable. The display device 7 is formed by use of a liquid crystal or organic electroluminescence (EL) monitor or the like.

A user observes a parallax image displayed on the display device 7 via glasses having a polarization capability. The user is thereby able to observe a stereoscopic image by observing an image for left eye with the user's left eye and observing an image for right eye with the user's right eye.

According to the above described first embodiment of the disclosure, the endoscope 2, the second processor 4, and the mixer unit 5 are synchronized with one another according to a synchronization signal generated by the synchronization signal generating unit 31 in the first processor 3. Accordingly, even if there is a difference between processing speeds of the first processor 3 and the second processor 4, the first processor 3 and the second processor 4 are able to be synchronized with each other. According to the first embodiment, synchronization is able to be achieved regardless of the volume of image data.

Second Embodiment

Figure 5:
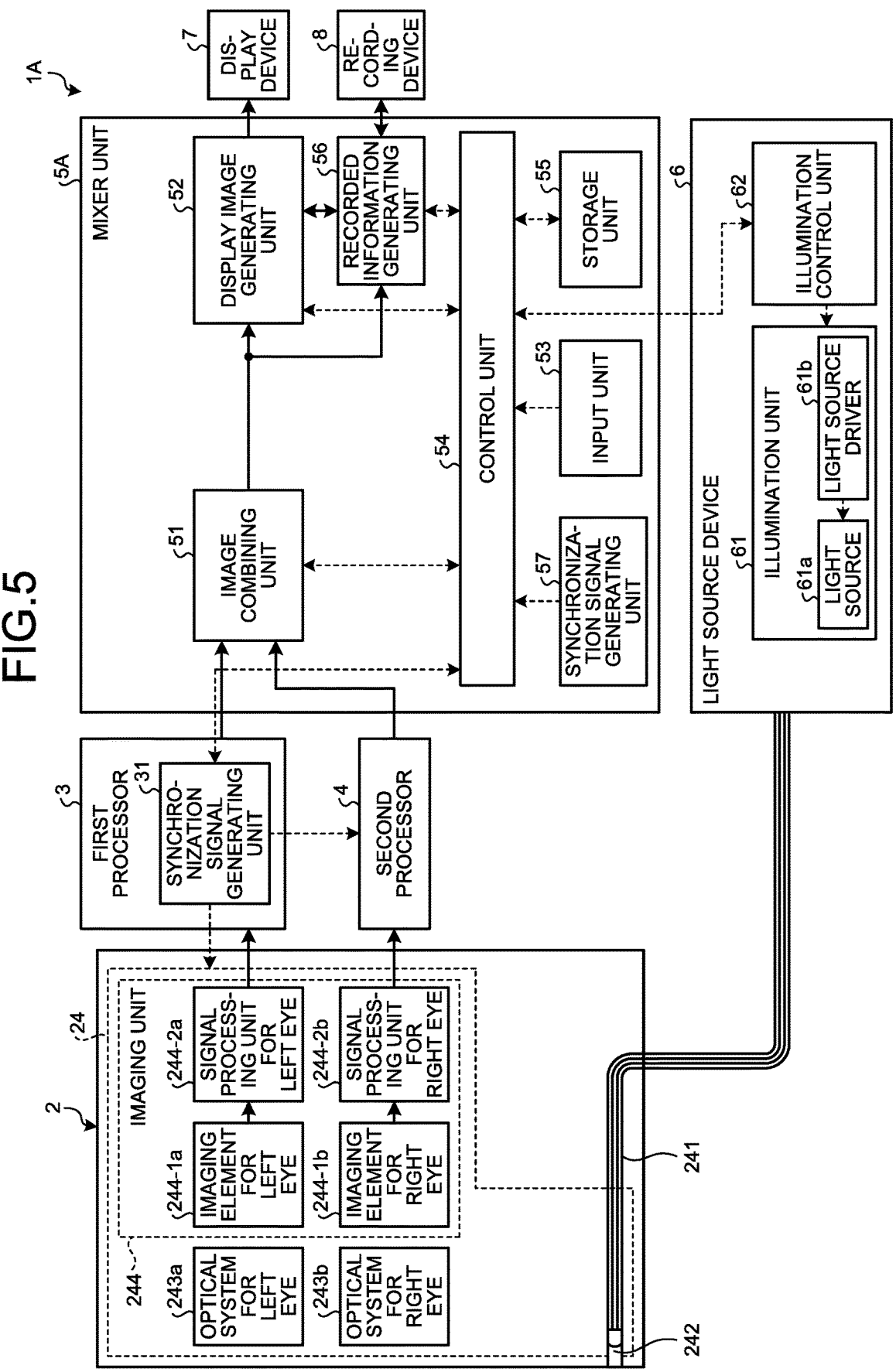
FIG. 5 is a block diagram illustrating a schematic configuration of an endoscope system according to a second embodiment of the disclosure.
Figure 6:
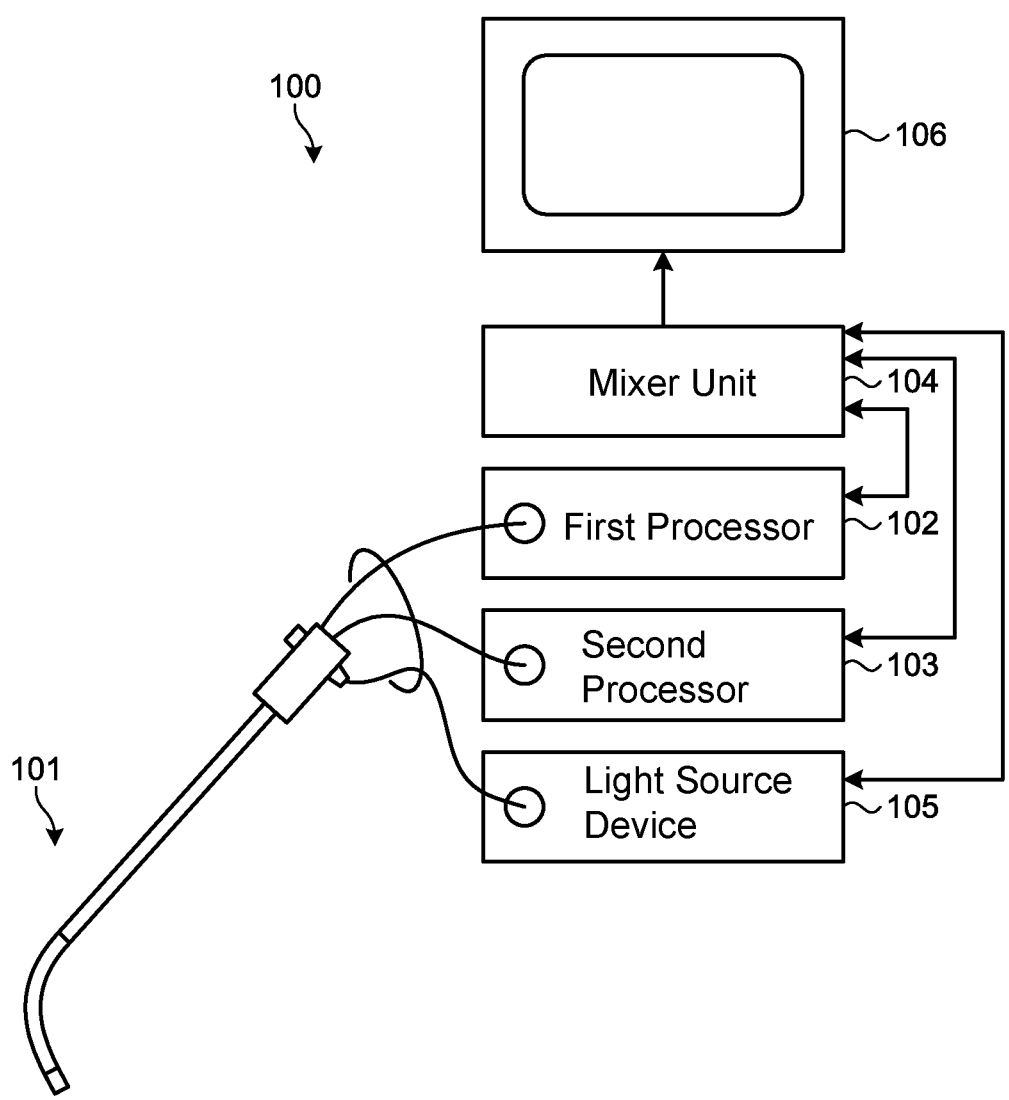
FIG. 6 is a diagram illustrating a schematic configuration of a conventional endoscope system.

Described next by reference to FIG. 5 is a second embodiment of the disclosure. According to this second embodiment, a synchronization signal generating unit is provided further in a mixer unit, in contrast to the above described configuration of the endoscope system 1. FIG. 5 is a block diagram illustrating a schematic configuration of an endoscope system according to the second embodiment of the disclosure. Described hereinafter are parts different from those of the above described configuration according to the first embodiment.

An endoscope system 1A illustrated in FIG. 5 include: the above described endoscope 2, first processor 3, second processor 4, light source device 6, and display device 7; a mixer unit 5A that performs predetermined signal processing on image data captured by the endoscope 2 and integrally controls operation of the whole endoscope system 1A; and a recording device 8 that records therein information generated by the mixer unit 5A. The recording device 8 records therein information acquired from the mixer unit 5A. The recording device 8 is formed by use of a computer readable recording medium, such as a hard disk, a flash memory, a CD-ROM, a DVD-ROM, or a flexible disk.

The mixer unit 5A further includes a recorded information generating unit 56 and a synchronization signal generating unit 57, in addition to the above described image combining unit 51, display image generating unit 52, input unit 53, control unit 54, and storage unit 55.

The recorded information generating unit 56 acquires combined image data generated by the image combining unit 51 and records the acquired combined image data into the recording device 8, and acquires information recorded in the recording device 8 and outputs the acquired information to the display image generating unit 52.

The synchronization signal generating unit 57 generates a clock signal (a synchronization signal) that serves as a reference for operation of the mixer unit 5A. The synchronization signal generated by the synchronization signal generating unit 57 includes a horizontal synchronization signal and a vertical synchronization signal.

In the endoscope system 1A, image data acquired by the endoscope 2 are received via the first processor 3 and second processor 4, and image data for display are generated therefrom and displayed on the display device 7; and in addition, information that has been recorded in the recording device 8, for example, combined image data, may be read out, the display image generating unit 52 may generate image data for display therefrom, and the image data for display may be displayed on the display device 7.

When image data to be displayed on the display device 7 are generated by use of information that has been recorded in the recording device 8, the image data are able to be acquired even if the first processor 3 has not been connected to the mixer unit 5A. However, when the mixer unit 5A has not been connected to the first processor 3, the mixer unit 5A is unable to receive a synchronization signal generated by the synchronization signal generating unit 31, and the devices are unable to be synchronized with one another by the synchronization signal generated by the synchronization signal generating unit 31. In this case, the control unit 54 realizes synchronization with the display device 7 by a synchronization signal generated by the synchronization signal generating unit 57. Accordingly, even if the first processor 3 is not connected to the mixer unit 5A, synchronization is achieved in the mixer unit 5A.

In the endoscope system 1A, when no signal has been input from the first processor 3 even if a preset time period elapses, for example, the control unit 54 determines that the first processor 3 has not been connected to the mixer unit 5A, and performs control such that a synchronization signal generated by the synchronization signal generating unit 57 is used. Instead, the synchronization signal generating unit 31 or 57 may be selected according to input of an instruction received by the input unit 53, or connection between the first processor 3 and the mixer unit 5A may be detected at a connecting portion between the first processor 3 and the mixer unit 5A. For example, a connection pin is provided in the first processor 3, a switch that is pushed down by the connection pin is provided in the mixer unit 5A, and the mixer unit 5A may recognize connection of the first processor 3 according to whether or not the switch for detection of connection has been pushed down by the connection pin.

According to the above described second embodiment, synchronization signals are generated by the synchronization signal generating unit 31 that the first processor 3 has and the synchronization signal generating unit 57 that the mixer unit 5A has. Accordingly, even if the first processor 3 is not connected to the mixer unit 5A, the mixer unit 5A is able to cause a display image to be displayed in synchronization with the display device 7, based on the synchronization signal generated by the synchronization signal generating unit 57.

According to the above description of the first and second embodiments, an image for left eye acquired by the imaging element for left eye and an image for right eye acquired by the imaging element for right eye are images having: a common object captured therein; object image acquisition areas that are partially different from each other; and a parallax from each other; but the image for left eye and the image for right eye may, for example, have the same field of view, and have illumination light wavelength bands different from each other or be based on light that has passed through filters having characteristics different from each other. As described above, the endoscope systems 1 and 1A according to the first and second embodiments enable the circuit scale of their processing devices to be decreased in their configurations for processing plural sets of image data where characteristics of their object images differ from one another at least partially. Furthermore, even in cases where signal processing is performed on images acquired by a binocular capsule-type endoscope, the images having different objects captured therein and different fields of view, the cases including a case where object image acquisition areas in the images are entirely different from one another; the circuit scale of the processing devices that perform processing on image data received from the capsule-type endoscope is able to be decreased.

The first processor 3 according to the above described first or second embodiment may have a control unit, which is provided in the first processor 3 and controls the whole endoscope system 1 or 1A like the control unit 54. Furthermore, according to the above description of the first and second embodiments, synchronization with the second processor 4 is achieved by a synchronization signal generated by the first processor 3, but a synchronization signal generating unit may be provided in the second processor 4, and synchronization with the first processor 3 may be achieved by a synchronization signal generated in the second processor 4.

Furthermore, in the above described first and second embodiments, transmission and reception of information between the endoscope 2 and the first processor 3 and second processor 4, and between the mixer unit 5 or 5A and the first processor 3 and second processor 4 may be performed by transfer by use of signal lines, by wireless communication, or by transfer via optical signals.

Moreover, according to the above description of the first and second embodiments, a simultaneous illumination/imaging system, in which white illumination light including RGB color components is emitted from the light source device 6 and the imaging elements receive reflected light arising from the illumination light, is adopted, but, for example, a field sequential illumination/imaging system, in which the light source device 6 sequentially emits light of the color components individually, and the imaging elements receive light of each color component, may be adopted instead.

In addition, according to the above description of the first and second embodiments, two imaging elements that respectively receive light from the optical system for left eye 243a and the optical system for right eye 243b are used in the configuration; but light may be received by: use of a single imaging element; and separation into an image generation area for left eye where light from the optical system for left eye 243a is received and an image generation area for right eye where light from the optical system for right eye 243b is received. In this case, a signal based on the light received at the image generation area for left eye is output to the first processor 3, and a signal based on the light received at the image generation area for right eye is output to the second processor 4.

What is more, in the above described first and second embodiments, the first processor 3 and the second processor 4 may be provided in housings separately bodied from each other, or may be provided in the same housing.

Furthermore, in the above described first and second embodiments, under control by the control unit 54, the display image generating unit 52 may generate image data for display, based on combined image data, according to a mode that has been set to one of: a mode where a three-dimensional image, such as the above described parallax image, is generated; and a mode where a two-dimensional image is generated by use of one of an image for left eye and an image for right eye that are included in the combined image data.

Moreover, according to the above description of the first and second embodiments, the light source device 6 is formed to be separately bodied from the endoscope 2, but a light source device may be provided in the endoscope 2 by, for example, provision of a semiconductor light source at a distal end of the endoscope 2.

In addition, according to the above description of the first and second embodiments, the light source device 6 is separately bodied from the mixer unit 5 or 5A, but the light source device 6 and the mixer unit 5 or 5A may be integrated with each other. What is more, the light source 61a may be provided at the distal end of the distal end portion 24.

Furthermore, according to the above description of the embodiments, in each of the endoscope systems 1 and 1A, targets to be observed are living tissues and the like in subjects, and the endoscope 2 that is flexible is used; but an endoscope system, in which a rigid endoscope, an industrial endoscope for observation of properties of materials, a capsule-type endoscope, a fiberscope, or a device having a camera head connected to an eyepiece unit of an optical endoscope, such as an optical visual tube, is used, may be adopted.

According to the disclosure, an effect of enabling synchronization regardless of the volume of image data is achieved.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system, comprising:
   a first processor configured to
      perform first image processing on a set of image data, and
      output the set of image data that has been subjected to the first image processing, the set of image data being one of: two sets of image data having object image acquisition areas that are at least partially different from each other; or two sets of image data having a parallax from each other for a common object;
   a second processor configured to
      perform second image processing on another set of image data, and
      output the other set of image data that has been subjected to the second image processing, the other set of image data being other one of: the two sets of image data having the object image acquisition areas that are at least partially different from each other; or the two sets of image data having the parallax from each other for the common object;
   a third processor that is provided in a housing separately bodied from a housing or housings where the first processor and the second processor are provided, the third processor being configured to generate, based on the set of image data output from the first processor and on the other set of image data output from the second processor, display image data to be displayed on a display;
   a recorder configured to record therein image data based on the set of image data output from the first processor and on the other set of image data output from the second processor;
   a fourth processor that is provided in the housing where the first processor or the second processor is provided, the fourth processor being configured to generate a first synchronization signal for synchronization among the first processor, the second processor, and the third processor;
   a fifth processor that is provided in the housing where the third processor is provided, the fifth processor being configured to generate a second synchronization signal for synchronization between at least the third processor and the recorder; and
   a controller configured to select one of the first synchronization signal generated by the fourth processor and the second synchronization signal generated by the fifth processor, and perform control for synchronization between the third processor and the recorder.

2. The endoscope system according to claim 1, wherein when the housing where the fourth processor is provided and the housing where the third processor is provided are electrically connected to each other, the controller is configured to select the first synchronization signal generated by the fourth processor.

3. The endoscope system according to claim 1, wherein when the housing where the fourth processor is provided and the housing where the third processor is provided are not electrically connected to each other, the controller is configured to select the second synchronization signal generated by the fifth processor.

* * * * *